US009849305B2

(12) United States Patent
Iwata

(10) Patent No.: US 9,849,305 B2
(45) Date of Patent: *Dec. 26, 2017

(54) TREATMENT PLANNING DEVICE, PARTICLE BEAM THERAPY SYSTEM AND METHOD FOR DETERMINING SCANNING ROUTE OF CHARGED PARTICLE BEAM

(71) Applicant: MITSUBISHI ELECTRIC CORPORATION, Chiyoda-ku, Tokyo (JP)

(72) Inventor: Takaaki Iwata, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 9 days.

This patent is subject to a terminal disclaimer.

(21) Appl. No.: 15/092,677

(22) Filed: Apr. 7, 2016

(65) Prior Publication Data

US 2016/0220843 A1  Aug. 4, 2016

Related U.S. Application Data

(63) Continuation of application No. 14/419,685, filed as application No. PCT/JP2012/080026 on Nov. 20, 2012, now Pat. No. 9,333,374.

(51) Int. Cl.
*G21G 5/00* (2006.01)
*A61N 5/00* (2006.01)
(Continued)

(52) U.S. Cl.
CPC ........... *A61N 5/103* (2013.01); *A61N 5/1031* (2013.01); *A61N 5/1043* (2013.01);
(Continued)

(58) Field of Classification Search
USPC ............. 250/370.09, 396 R, 492.22, 492.21, 250/492.3, 526; 378/64, 65, 95, 96, 113,
(Continued)

(56) References Cited

U.S. PATENT DOCUMENTS 6,546,073 B1 * 4/2003 Lee ...................... A61N 5/1031
378/65
8,106,371 B2 * 1/2012 Fujii .................... A61N 5/1044
250/492.3
(Continued)

FOREIGN PATENT DOCUMENTS

JP  2007-514499 A  6/2007
JP  2009-066106 A  4/2009
(Continued)

OTHER PUBLICATIONS

International Search Report (PCT/ISA/210) dated Dec. 25, 1012, by the Japanese Patent Office as the International Searching Authority for International Application No. PCT/JP2012/080026.
(Continued)

*Primary Examiner* — Bernard Souw
(74) *Attorney, Agent, or Firm* — Buchanan Ingersoll & Rooney PC

(57) ABSTRACT

A scanning candidate route extracting unit which extracts plural candidates of scanning routes in which each of the scanning routes connects all spot positions in one layer is provided, in an evaluation function using necessary scanning time Tk and weight coefficient wk for a kth partial route among partial routes which are routes between the spot positions which are adjacent on one of the plural candidates of scanning routes, and number n of spot in the layer, wk with respect to a partial route which passes through affected tissue is set to be 1, wk with respect to a partial route which passes through normal tissue is set to be bigger than 1, and wk with respect to a partial route which passes through an
(Continued)

important internal organ is set to be bigger than wk with respect to a partial route which passes through normal tissue.

9 Claims, 7 Drawing Sheets

(51) Int. Cl.
    *A61N 5/01*         (2006.01)
    *A61N 5/10*         (2006.01)

(52) U.S. Cl.
    CPC ......... *A61N 5/1044* (2013.01); *A61N 5/1077* (2013.01); *A61N 2005/1074* (2013.01); *A61N 2005/1087* (2013.01)

(58) Field of Classification Search
    USPC ................................. 378/145, 146, 210, 901
    See application file for complete search history.

(56) References Cited

U.S. PATENT DOCUMENTS

| | | | | |
|---|---|---|---|---|
| 8,565,378 | B2* | 10/2013 | Echner | A61N 5/1042 378/148 |
| 8,847,179 | B2* | 9/2014 | Fujitaka | A61N 5/1036 250/492.1 |
| 9,333,374 | B2* | 5/2016 | Iwata | A61N 5/103 |
| 2008/0226029 | A1* | 9/2008 | Weir | A61B 1/07 378/65 |
| 2010/0117002 | A1* | 5/2010 | Rinecker | A61N 5/103 250/396 R |
| 2010/0187435 | A1* | 7/2010 | Iseki | A61N 5/1043 250/398 |
| 2010/0243911 | A1 | 9/2010 | Fujii et al. | |
| 2011/0280372 | A1* | 11/2011 | Ivanov | A61N 5/103 378/65 |
| 2012/0187314 | A1 | 7/2012 | Bert et al. | |
| 2012/0228521 | A1* | 9/2012 | Honda | A61N 5/1043 250/492.3 |
| 2012/0264998 | A1* | 10/2012 | Fujitaka | A61N 5/1036 600/1 |

FOREIGN PATENT DOCUMENTS

| | | |
|---|---|---|
| JP | 2010-253250 A | 11/2010 |
| JP | 2012-223259 A | 11/2012 |
| WO | WO 2011/142442 A1 | 11/2011 |

OTHER PUBLICATIONS

Joanne H. Kang et al., "Demonstration of Scan Path Optimization in Proton Therapy", Med. Phys., vol. 34, No. 9, Sep. 2007, pp. 3457-3464.

Office Action (Notice of Reasons for Refusal) dated Dec. 6, 2016, by the Japanese Patent Office in corresponding Japanese Patent Application No. 2016-016841 and partial English translation of the Office Action. (4 pages).

* cited by examiner

TREATMENT PLANNING DEVICE, PARTICLE BEAM THERAPY SYSTEM AND METHOD FOR DETERMINING SCANNING ROUTE OF CHARGED PARTICLE BEAM

TECHNICAL FIELD

This invention relates to a scanning type particle beam therapy system which is used for cancer therapy, etc. and a treatment planning device of the particle beam therapy system.

BACKGROUND ART

Radiation which is used for cancer therapy is broadly divided into two groups, that is, a photon beam and a particle beam. A photon beam is a wave of light and is used as conventional radiation such as X-ray, gamma rays, etc. On the other hand, a particle beam is radiation which is made by utilizing a particle of an atomic nucleus of hydrogen or that of carbon, etc. Especially, in the medical field, a beam, which is obtained by accelerating 'a proton' which is obtained by ionizing a hydrogen atom or 'a carbon ion' (will be also referred as a heavy ion) which is obtained by ionizing a carbon atom, is mainly used.

A particle beam therapy is based on the following principle. When a cancer cell is irradiated by a particle beam, DNA of the cancer cell is damaged, and the cell which is damaged to the degree which is beyond its own repair ability gradually dies and eventually, will be discharged from the body. A photon beam type conventional radiation, such as X-ray, gamma rays, etc. acts along the surface of a body. On the other hand, a particle beam has the feature such that the absorbed dose reaches a peak just before when the particle beam stops. Therefore, by changing a level of energy, a position where the absorbed dose reaches a peak (will be referred as a Bragg peak) can be focused on cancer nidus. Consequently, only the cancer nidus can be intensively destroyed. As above mentioned, more excellent effect than that of conventional technology can be obtained. Consequently, a particle beam therapy is expected increasingly as a therapy which can maintain QOL (Quality of Life).

In order to effectively perform a particle beam therapy, it is necessary to form a beam while damage is not given to surrounding tissue and sufficient level of dose is given to affected tissue. An irradiation method for realizing the beam forming is divided broadly into a 'broad beam irradiation method' and a 'scanning irradiation method'. The broad beam irradiation method is a method in which a beam which is enlarged once by using a scattering body or a ridge filter, etc. is formed by using a collimator or a bolus. On the other hand, the scanning irradiation method is a method in which a pencil beam which is a beam whose beam diameter is kept to be small is scanned so as to scan in a pointillist manner (spot scanning having ON/OFF of beam) or so as to scan in a one-stroke sketch manner (raster scanning: beam is ON in principal).

Here, regarding scanning irradiation, more details will be described, and a relationship with a treatment planning device will be described. As described in the above, a particle beam has the feature such that a particle beam has a Bragg peak having a depth which corresponds to a level of energy. In order to apply appropriate irradiation dose to tissue of an affected part having a depth in intra-corporeal direction, it is assumed such that the tissue of an affected part is virtually divided into a layer which corresponds to a level of beam energy, the above-mentioned spot scanning or raster scanning is performed for each layer. Regarding a Bragg peak of a particle beam, an amount of dose which is applied to a side which is deeper than the Bragg peak is approximately zero. However, to a side which is shallower than the peak, some dose is applied. Therefore, considering the effect, at each spot position of each layer, irradiation amount should be determined. A treatment planning device calculates or simulates for determining an irradiation amount of the each spot for the each layer in order to realize to apply appropriate dose based on information of three dimensional image of an affected part which was photographed in advance.

In performing actual scanning irradiation, there is another thing to be determined; sequence order of irradiating each spot at each layer, that is, how a scanning route is determined. In a raster scanning, when it is assumed such that irradiation is performed by following a track which is made by combining each spot, the above-mentioned can be applied. In general, a treatment planning device performs a function of determining the scanning route of scanning. Prior art regarding the scanning route of the scanning is disclosed in Patent Document 1 or Non-Patent Document 1.

PRIOR ART REFERENCE

Patent Document

Patent Document 1: JP2009-66106A

Non-Patent Document

[Non-Patent Document 1]
J. H. Kang et al., "Demonstration of scan path optimization in proton therapy" Medical Physics 34(9)2007, page 3457-3464

DISCLOSURE OF THE INVENTION

Problems to be Solved by the Invention

Non-Patent Document 1 discloses a method to extract a route whose distance of scanning route is short. However, as will be described later, the distance of a route and time which is required for scanning does not correspond each other. Consequently, as an evaluation in which a distance of a route is an indicator, a scanning route whose scanning time is optimized is not always selected. In light of the above-mentioned problem, an objective of this invention is to obtain a treatment planning device for obtaining a scanning route in which scanning time in a raster scanning type particle beam therapy system is shortened and avoiding of irradiation to normal tissue and important organs is considered, and a particle beam therapy system in which the above-mentioned scanning route is utilized.

Means for Solving the Problems

According to this invention, a treatment planning device, by which a scanning route of a charged particle beam of a particle beam therapy system is determined, wherein the particle beam therapy system comprises an X-directional scanning electromagnet and a Y-directional scanning electromagnet for deflecting a charged particle beam in an X-direction and a Y-direction which are two perpendicular directions to a traveling direction of the charged particle beam so as for the charged particle beam to move and stay repeatedly and the charged particle beam is irradiated onto an affected part of a patient which is an irradiation objective, comprises a spot position storing unit which stores spot positions which are arranged in a grid shape in the X-direction and the Y-direction for each layer, which are points set in the affected part where the charged particle beam stays, a scanning candidate route extracting unit which extracts plural candidates of scanning routes in which each of the scanning routes connects all spot positions in one layer which are stored in the spot position storing unit, a scanning route evaluating unit which defines an evaluation function J $$J = \sum_{k=1}^{n-1} (w_k T_k)$$

using necessary scanning time Tk and weight coefficient wk for a kth partial route among partial routes which are routes between the spot positions which are adjacent on one of plural scanning routes which are extracted by the scanning candidate route extracting unit, and number n of spots in the layer, and calculates the evaluation function J regarding each of plural scanning candidate routes which are extracted by the scanning candidate route extracting unit by setting a weight coefficient wk with respect to a partial route which passes through affected tissue to be 1, the weight coefficient wk with respect to a normal tissue to be larger than 1 and the weight coefficient wk with respect to a partial route which passes through an important internal organ to be larger than the weight coefficient wk with respect to a partial route which passes through the normal tissue and a scanning route determining unit which determines a scanning route which is used for therapy based on a value of the evaluation function J which is calculated by the scanning route evaluating unit.

Advantage of the Invention

According to a treatment planning device of this invention, a particle beam therapy system in which irradiation risk of charged particle beams for other than affected tissue is small, and whole of irradiation time is short can be provided.

EMBODIMENTS FOR CARRYING OUT THE INVENTION

Figure 1:
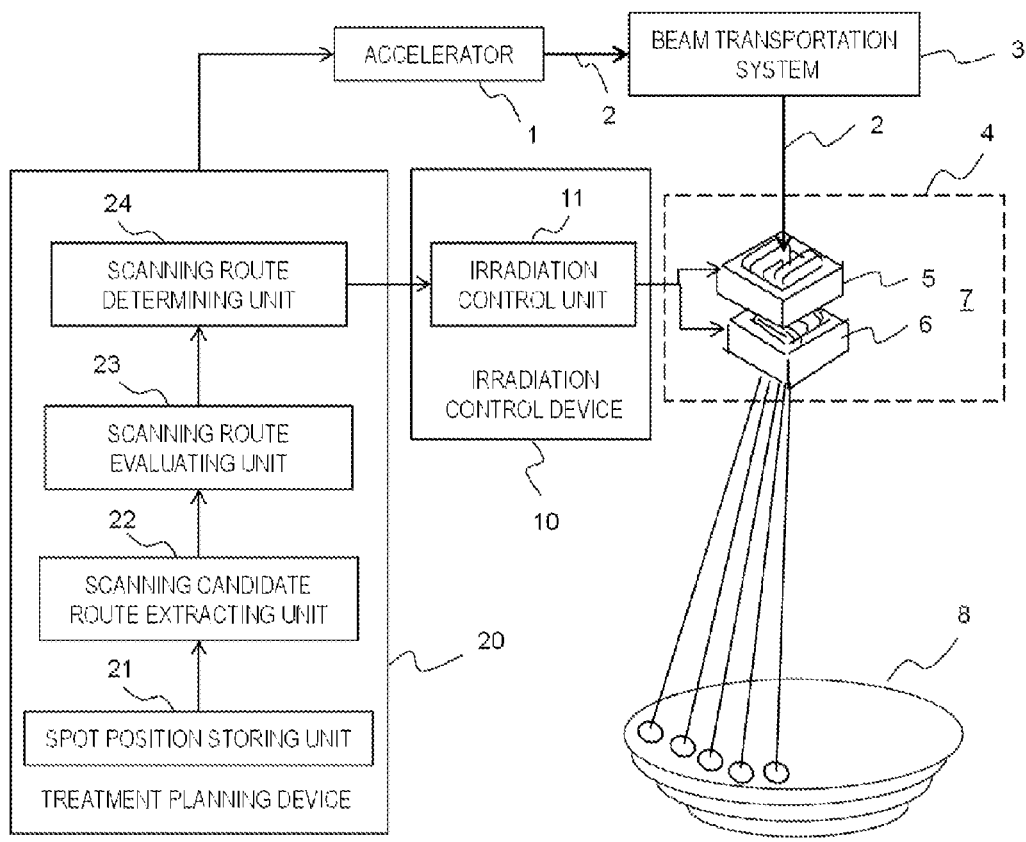
FIG. 1 is a block diagram showing the configuration of a particle beam therapy system including a treatment planning device according to Embodiment 1 of this invention.

A problem for determining a route by giving a point which has to be passed is formulated as Traveling Salesman Problem, TSP. Typical Traveling Salesman Problem will be described in the following. Typical Traveling Salesman Problem is optimization of combination, that is, when gathering of cities and traveling cost between individual two cities (for example, distance) is given, a case in which whole traveling cost of circuit route in which all cities are visited once to return to a starting point is smallest (shortest route is obtained in a case where a salesman visits predetermined cities once) is obtained.

Consequently, regarding a scanning irradiation type of a particle beam therapy system, in determining a route for scanning a beam, it is assumed such that by simply applying to the above-mentioned Traveling Salesman Problem, by using a tool for solving the existing Traveling Salesman Problem, a route whose distance is shortest may be obtained. However, regarding a method for obtaining a route whose distance is shortest has the following problems.

In general, scanning of a pencil beam of a particle beam is realized by two scanning electromagnets for an X-directional deflection and for a Y-directional deflection. It is necessary to arrange a scanning electromagnet on a beam path, however, it is physically impossible to provide a scanning electromagnet for an X-directional deflection and a scanning electromagnet for a Y-directional deflection at the same position. A scanning electromagnet for an X-directional deflection and a scanning electromagnet for a Y-directional deflection are arranged on a beam path in parallel. As a result, a distance from an isocenter which is an irradiation reference point to a scanning electromagnet for an X-directional and that to a scanning electromagnet for a Y-directional deflection are different, and sizes of the electromagnets are different. Consequently, a scanning speed in an X-direction is different from that in a Y-direction. Therefore, there is a problem such that even when 'a route whose distance is shortest' is obtained, the obtained route is not a case in which scanning time (therapy time) is smallest.

Regarding the above-mentioned problem, it may be assumed such that a scanning area may be converted by a coordinate transformation based on scanning speed in an X-direction and that in a Y-direction. For example, in a case where the scanning speed in an X-direction is 1, and the scanning speed in a Y-direction is 2, when the scanning area is expanded twice in a Y-direction, it is assumed such that a route whose distance is shortest in the scanning area which was converted by a coordinate transformation will be equal to a route whose required time is shortest.

However, the above-mentioned technique of coordinate transformation dose not solve the problem. That will be clear by examining the following simple example. As described in the above, in a particle beam therapy system, scanning of abeam is performed by independent scanning electromagnets in an X-direction and in a Y-direction, respectively. As a result, in a case where change is made both in an X-direction and a Y-direction where a point of scanning of a beam is a starting point, a scanning time is not proportional to a scanning distance, and a scanning time has a feature such that the scanning time will be a scanning time in an X-direction or a scanning time in a Y-direction which is longer. (For example, in a case where both of scanning speed in an X-direction and that in a Y-direction is 1, a distance in a case where a charged particle beam is moved in an X-direction by 1 and is moved in a Y-direction by 1 will be √2, however, a scanning time will be 1).

In a raster scanning, there is another problem such that it is not sufficient only to select a route whose distance is shortest. As described in the above, in a scanning irradiation method, affected tissue is divided into a layer and a beam is scanned for each layer. Even in a case where affected tissue which is an irradiation object is one closed region, as a result of dividing the closed region into a layer, there is a case where in some layer, an irradiation region may be plural closed regions. From a mathematical view point, in a case where affected tissue which is an irradiation objective is not bounded convex set, the above-mentioned phenomenon will occur. In a case where irradiation regions in a layer are plural closed regions, when a beam moves between the regions, a region other than the irradiation region will be irradiated. By simply obtaining a route whose distance is shortest or a route whose required time is shortest, influence to a region other than the irradiation region will not be considered. Further, there is a problem such that even in a case where an area which has an important organ, etc., should be extremely avoided to irradiate, the above-mentioned influence is not considered.

As a result of dividing affected tissue which is an irradiation objective into a layer, even when an irradiation region in a layer is one, the irradiation region is not convex set. When an irradiation region is not convex set, some of the obtained route may pass through normal tissue or an important organ.

As it is named to be 'traveling', the Traveling Salesman Problem regards to optimization regarding 'loop' in which a starting point coincides with an end point. On the other hand, regarding a problem of scanning route of a raster scanning, it is not always necessary for a starting point to coincide with an end point. That is, a scanning route of a beam regards to optimization of not 'a loop' but 'a route'. However, when most suitable loop can be obtained, there is a merit such that all spots can be selected as a starting point. The inventor of this invention present the above-mentioned problem for the first time, in this invention, solution for solving the above-mentioned problem will be proposed.

Embodiment 1

FIG. 1 is a block diagram for showing the configuration of a particle beam therapy system including a treatment planning device according to Embodiment 1 of this invention. In FIG. 1, a charged particle beam 2 such as a proton, a carbon ion beam, etc. is outputted from an accelerator 1 and the charged particle beam 2 is guided to a beam irradiation system 4 by a beam transportation system 3 comprising a group of electromagnet, etc. At the beam irradiation system 4, a set of scanning electromagnet 7, comprising an X-directional scanning electromagnet 5 which deflects an incident charged particle beam 2 in two dimensions, that is, X-Y directions which are vertical to a traveling direction of the charged particle beam 2, is provided. The scanning electromagnet 7 deflects the charged particle beam 2 so as to move and stay repeatedly in an X-direction and a Y-direction which are vertical to a traveling direction of the charged particle beam and scan. In this time, while the charged particle beam 2 moves, the charged particle beam 2 irradiates. On the other hand, in a treatment planning device 20, an irradiation plan for a target 8 which is an affected part of a patient is made. Specifically, by scanning a position of a Bragg peak which is formed by the charged particle beam 2 along the three-dimensional configuration in three-dimensional volume region of the target 8, in order to form a dose region which conforms to a shape of a target, a spot position where a charged particle beam stays in the target 8 and an amount of irradiation dose at each spot position will be determined. At the same time, among the group of spot position, a set of spot positions which corresponds to same energy of particle beam is stored as spot positions in a layer existing in one layer is stored in a spot position storing unit 21 for each layer.

In a scanning candidate route extracting unit 22, based on spot positions which are stored in the spot position storing unit 21, plural candidate scanning routes for each layer will be extracted. A method for extracting a scanning candidate route will be described in Embodiment 2. An objective of this invention is to determine a route in which required time for scanning is short and a scanning route where the beam will not pass through an important internal organ while the beam moves between spots, among the candidate scanning routes for each layer. Consequently, in order to extract a route where a beam will not pass through an important internal organ and in which required time for scanning is short among the candidate scanning routes, following evaluation function regarding a scanning route will be introduced.

Evaluation function J will be defined as follows.

$$J = \sum_{k=1}^{n-1} (w_k T_k)$$

Tk: time which is required for scanning a beam from a spot which is selected as kth spot to a spot which is selected as k+1th spot (hereinafter, will be referred to as a kth partial route)

wk: weight coefficient with respect to kth partial route

In a case where a kth partial route is included in affected tissue, wk=wkd=1.

In a case where a partial route of kth route passes through normal tissue, wk=wko>1.

In a case where a kth partial route passes through an important internal organ, wk=wkO>wko.

Figure 2:
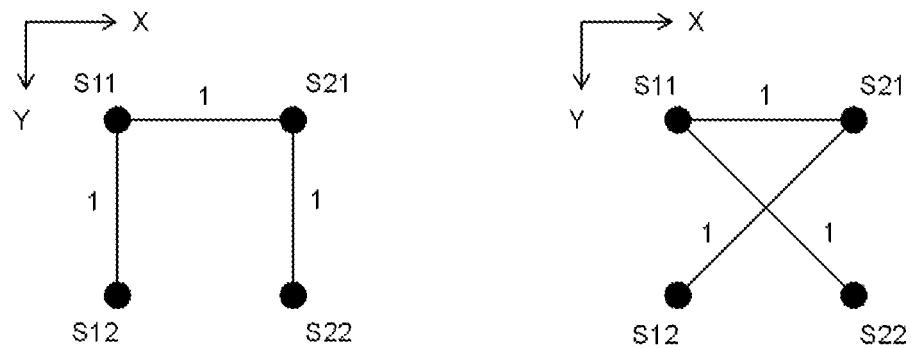
FIG. 2 is a layout drawing showing spot positions and a scanning routes for describing this invention.

In FIG. 2, for simplification, spots which are arranged in a grid shape of 2×2 are indicated by a black circle. Further, for simplification, a scanning time to a spot which is adjacent in an X-direction is set to be 1, and in the same way, a scanning time to a spot which is adjacent in a Y-direction is set to be 1. Here, we should keep in mind such that scanning time to a spot which is in an oblique direction is not √2 but 1. As described in the above, this is because scanning in an X-direction and scanning in a Y-direction is performed independently and simultaneously. Consequently, Tk in a route from S11 to S21 and Tk in a route from S11 to S22 are set to be a same value. As described in the above, a first point of this invention is such that not a length of a route but time which is required for scanning a beam regarding a route is evaluated.

Further, it is necessary to keep in mind such that an evaluation function is time which is spent for scanning a beam and is not time which is spent for actual irradiation. In actual irradiation, target dose which is obtained by a therapy plan at each spot has to be applied, this is because such that a charged particle beam moves and stays repeatedly. In order to distinguish the above-mentioned irradiation method from conventional raster scanning in which scanning is performed at a fixed speed, in some cases, the above-mentioned irradiation method may be referred to as hybrid scanning.

Figure 3A:
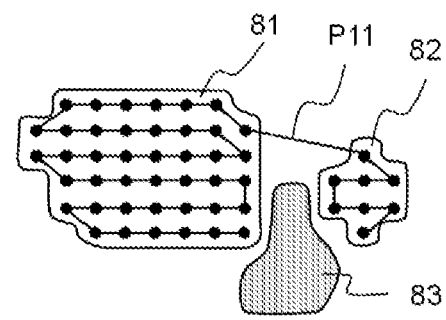
FIG. 3A and FIG. 3B are layout drawings showing examples of spot positions and scanning routes for describing this invention.
Figure 3B:
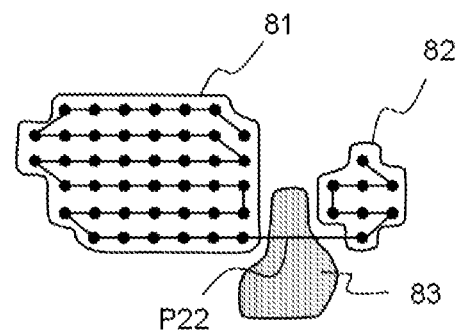

On the other hand, in a case where a route passes through not affected tissue but normal tissue, further in a case where a route passes through an especially important internal organ among normal tissue, since the risk of the route is large, weight coefficient is made to be large. For example, as shown in FIG. 3A and FIG. 3B, in a case where an affected part is a separated region such as an affected part 81 and an affected part 82, a part of a partial route passes through a region other than an affected part. A case in which an important internal organ exists between affected parts may be assumed. As described in the above, in a case where the partial route is included in affected tissue, weight coefficient wk is set to be 1, in a case where the partial route passes through not affected tissue but normal tissue, weight coefficient wk is set to be bigger than 1 and in a case where the partial route passes through the important internal organ 83 which is not affected tissue, weight coefficient wk is set to be much bigger value. By setting weight coefficient wk as described in the above, a value of evaluation function J of a candidate scanning route which includes a partial route P22 which passes through the important internal organ such as a scanning route in FIG. 3B is bigger than that of a candidate scanning route which includes a partial route P11 which passes through normal tissue such as a scanning route in FIG. 3A.

A scanning route evaluating unit 23 calculates a value of an evaluation function J regarding each of plural candidate scanning routes which are extracted by the scanning candidate route extracting unit 22. A scanning route determining unit 24 determines a candidate scanning route whose value of an evaluation function J is small, among candidate scanning routes, based on a value of an evaluation function J which is calculated by the scanning route evaluating unit 23, as a scanning route for using irradiation for therapy. An irradiation control part 11 of an irradiation control device 10 controls the X-directional scanning electromagnet 5 and the Y-directional scanning electromagnet 6 so as for the charged particle beam 2 to move according to the scanning route which is determined by the scanning route determining unit 24.

According to the above-mentioned configuration, a particle beam therapy system whose scanning time is short, and risk of irradiation to normal tissue, especially important internal organ is small can be obtained.

Embodiment 2

Depending on a size of affected tissue which is an irradiation object, consistently, a number of spot for one layer is in a range between several thousands and several ten thousands. Even in a case where a number of spot is only ten, in order to obtain an appropriate route which minimizes an evaluation function, 10!=3,628,800 kinds of evaluation function have to be calculated. Therefore, it is not practical to perform all of kinds forcefully. Consequently, in Embodiment 2, the peculiarities of canning irradiation in a particle beam therapy is considered and a method for determining most optimal or quasi-optimal scanning route mechanically will be described.

As described in the above, a scanning irradiation in a particle beam therapy is managed by unit which is referred to as "spot" in an irradiation region of each layer, commonly, the spots are arranged in a reticular pattern. As described in FIG. 2, regarding spots which are arranged in a reticular pattern of 2×2, a scanning time to a spot which is adjacent in an X-direction is set to be 1, and in the same way, a scanning tome to a spot which is adjacent in a Y-direction is set to be 1. Here, we should keep in mind such that scanning time to a spot which is in an oblique direction is not √2 but 1. When we keep in mind the above-mentioned, following theorems will be derived.

(Theorem 1)

Regarding one or plural spots which are arranged in a grid shape, in a case where a scanning time to a spot (point of intersection) which is adjacent in an X-direction is set to be 1, and in the same way, a scanning time to a spot which is adjacent in a Y-direction is set to be 1, a scanning time according to a scanning route where all spots are passed through is n−1 or more. Here, n indicates total number of n.

(Theorem 2)

Regarding one or plural spots which are arranged in a grid shape, in a case where a scanning time to a spot (point of intersection) which is adjacent in an X-direction is set to be $T_{min\_x}$, a scanning tome to a spot which is adjacent in a Y-direction is set to be $T_{min\_y}$, ($T_{min\_y} > T_{min\_x}$) a scanning time according to a scanning route where all spots are passed through is $(l-1) T_{min\_y}+(n-1) T_{min\_x}$ or more. Here, l indicates a number of rows at which spots are arranged. Further, necessary conditions for existence of a scanning route where a scanning time according to a scanning route where all spots are passed through is $(l-1) T_{min\_y}+(n-1) T_{min\_x}$ is as follows.

Condition 1: An irradiation region is one closed region and

Condition 2: An irradiation region is Convex in an X-direction.

Here, "Convex in an X-direction" means the state in which in a case where each row of grid is observed, at all rows where spots exist, a group of spots which are arranged adjacently is one.

Theorem 1 expresses relationship between a number of spot and shortest time for scanning all spots in a case where spots are arranged in a grid shape. When a case in which plural spots are arranged adjacently in one row is assumed, it is easily found out such that the shortest time is n−1.

In the same way of theorem 1, theorem 2 describes the relationship between a number of spot and the shortest time, however, the difference of scanning time in an X-direction and a Y-direction is considered. As it is supposed according to theorem 2, in a case where scanning time in an X-direction is shorter than that in a Y-direction, regarding a route in which all spots are scanned in the shortest time, a candidate route is a route in which (a) a point which is left end (or right end) on a top row (or a bottom row) which is set to be a starting point, (b) scanning is performed to other end in an X-direction, that is, "row" is scanned (c) so as to move to an end of following row. At this time, when spots are adjacent at all times (side to side, up-down, obliquely), this is the shortest-time route. For simplification, the above-mentioned scanning route will be referred to as "zigzag route". When a scanning time in a Y-direction is short, the Y-direction is set to be as a row direction, a route may be determined based on the idea which is same as the above-mentioned.

Figure 6:
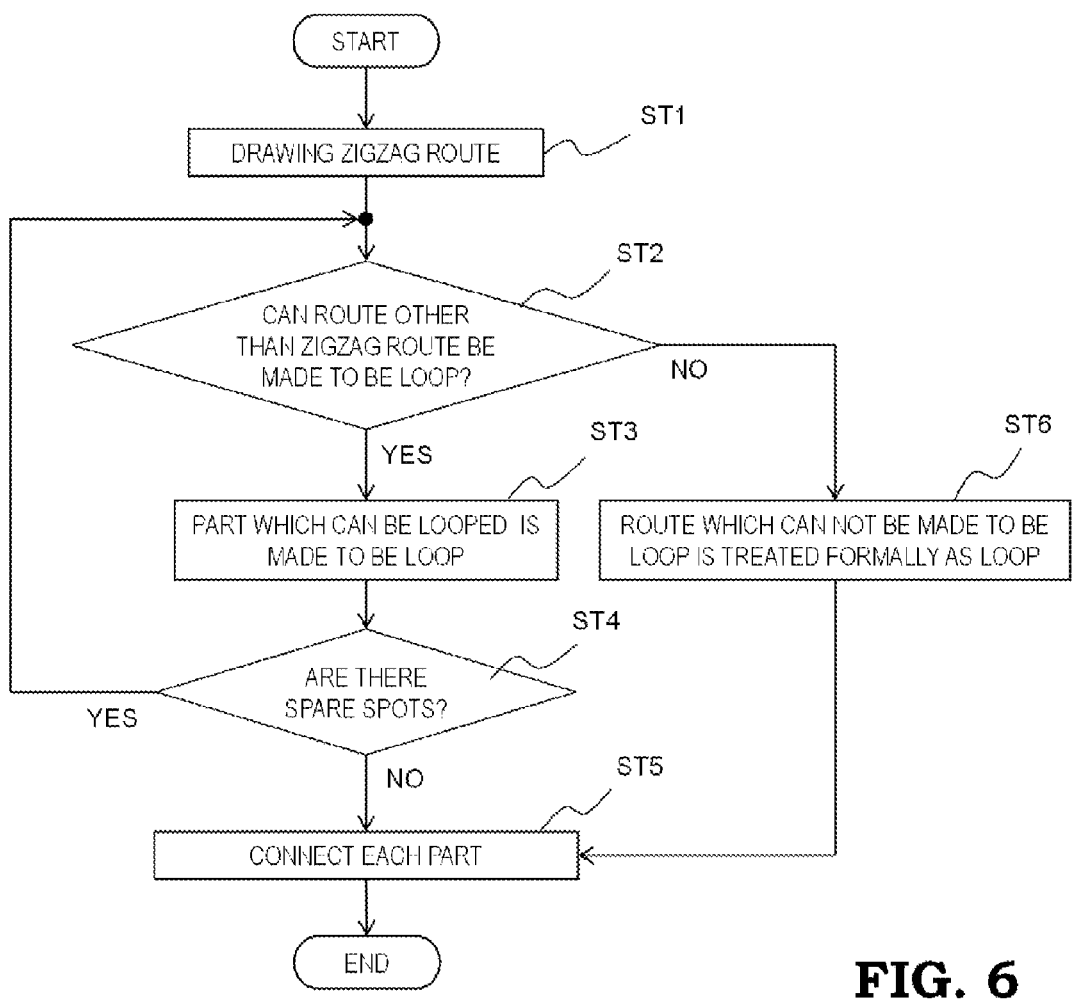
FIG. 6 is a flow chart showing steps of a treatment planning device according to Embodiment 2 of this invention.

As a matter of course, in some shapes of affected tissue which is an irradiation object, there are some cases when all spots cannot be scanned by the zigzag route. Therefore, here, referring conceptual diagrams of FIG. 4 to FIG. 7 and flow chart of FIG. 6, a method for determining a scanning route in the above-mentioned cases will be described.

Figure 4:
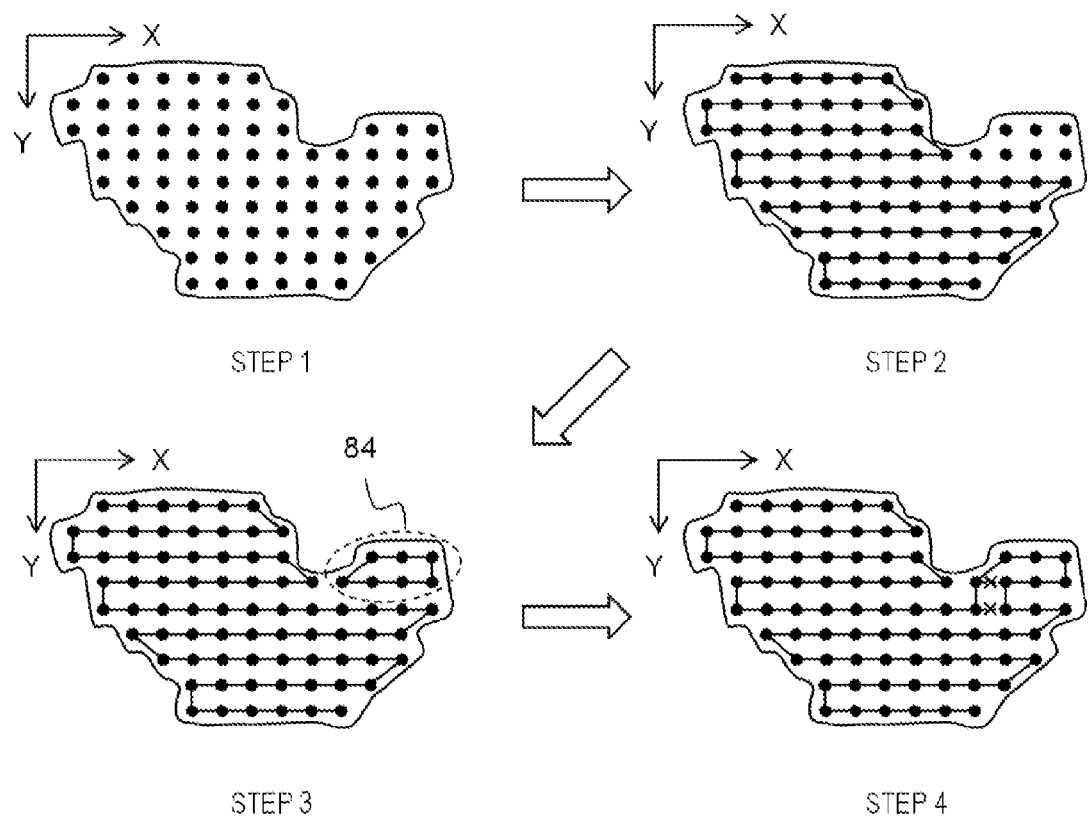
FIG. 4 is a layout drawing showing another example of a spot position and a scanning route for describing this invention.
Figure 5:
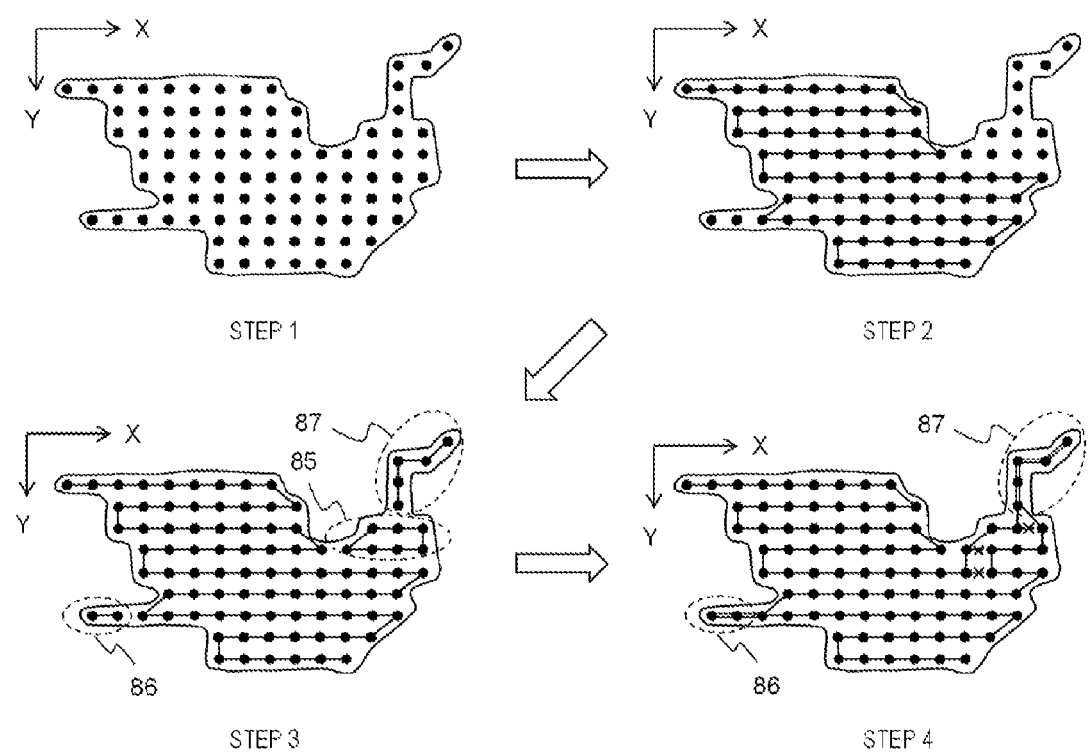
FIG. 5 is a layout drawing showing another example of a spot position and a scanning route for describing this invention.

FIG. 4 shows a method for determining a scanning route by dividing into four steps.

Step 1: An irradiation region in a layer and spot are shown.

Step 2: From the above-mentioned starting point (here, from the left end on the uppermost row), a part in which a zigzag route can be drawn is drawn (regarding zigzag route, partial optimal) (ST1).

Step 3: Regarding a route other than the zigzag route, whether optimization can be made or not is examined (ST2). When the part other than the zigzag part is made to be a loop in the same as that which is indicated by a group of spot 84 in FIG. 4 (ST2, YES, ST3), regarding a part of a loop, procedure will be moved to Step 4.

Step 4: When the zigzag route and a loop of Step 3 adjoins each other through two adjacent spots, the zigzag route and the loop will be connected as shown in FIG. (ST4 NO, ST5). When there are spare spots, procedure will be returned to Step 3 (ST4 YES).

There are some cases which cannot always be solved according to a method shown in FIG. 4 (ST2 NO). This is a case where a group of spots in a part other than a zigzag route are arranged in one dimension and is not a loop. In Step 3 shown in FIG. 5, routes including a group of spot 85 in which other part is a loop, a group of spot 86 which are arranged in one dimension and a group of spot 87 exist. In the above-mentioned case, treating formally the above-mentioned route as a loop will be considered (ST6). "Treating formally as a loop" means such that as shown in the figure of Step 4 in FIG. 5, a route is set by a round-trip route with regard to a group of spots which are arranged in one dimension. In this case, same spot is passed twice, in the spot, time for a charged particle beam to stay may be divided so as for an amount of irradiation dose of two irradiation to be the target dose of therapy plan. A method in which an amount of irradiation dose to be divided and plural irradiation is performed is well known and referred to as "repaint irradiation". In this invention, "partial repaint" method in which only remaining route is repainted will be proposed. Using a part which is formally treated as a loop, a zigzag route is connected to the loop (ST 5).

Figure 7:
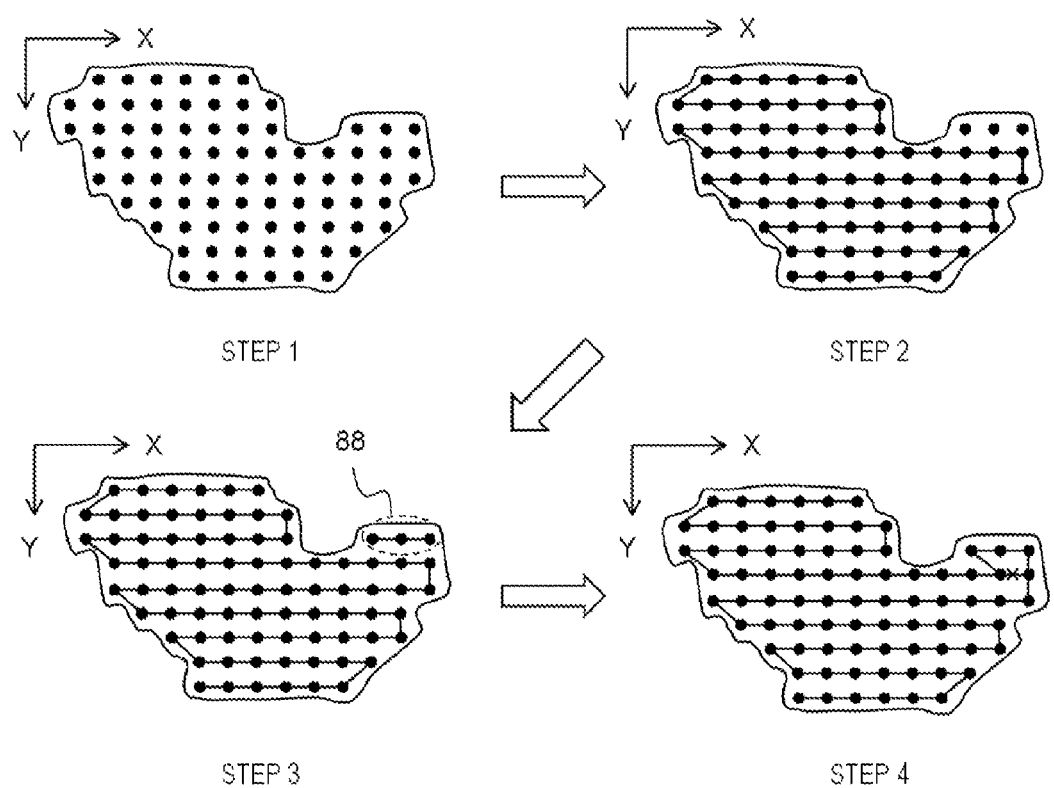
FIG. 7 is a layout drawing showing an example in which a spot position is same as that in FIG. 4 and a scanning route is different from that in FIG. 4.

Next, in a spot position shown in FIG. 4, a candidate scanning route in a case where a starting point is changed will be described. FIG. 7 shows a candidate scanning in a case where a left end in the lowermost row is a starting point. First, as Step 2, a zigzag route is drawn from a starting point. In Step 3, regarding a spot group 88 of remaining part, route is drawn. The spot group 88 is a spot group in which spots are arranged in one dimension. In Step 4, the zigzag route which is drawn in Step 2 is connected to the route which is drawn in one dimension in Step 3.

Figure 8:
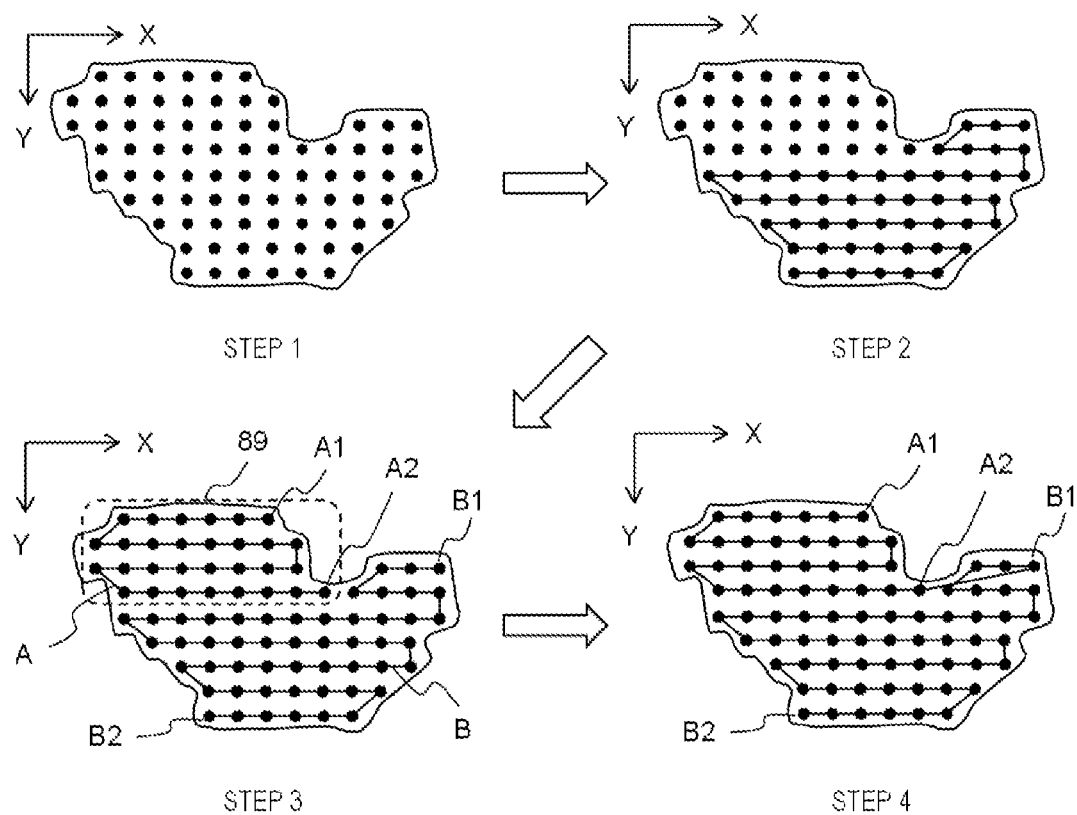
FIG. 8 is a layout drawing showing an example in which a spot position is same as that in FIG. 4 and a scanning route is different from that in FIG. 4 and that in FIG. 7.

FIG. 8 is a candidate scanning route in a case where a starting point is a right end of uppermost row in a right-side region. First, as Step 2, a zigzag route is drawn from a starting point. In Step 3, regarding a spot group 89 of remaining part, an optimal route is drawn. Here, a zigzag route can be drawn, therefore a zigzag route will be drawn. In Step 4, two zigzag routes are connected.

In a case where plural zig-zag routes are drawn, ends of zigzag routes are connected in series that is, a partial route is connected in parallel finally, the plural zigzag routes should be one route. In this case, several combinations, that is, which end is a starting point, can be assumed. As shown in FIG. 8, two partial routes A and B exist, ends of the partial route A is set to be A1 and A2, respectively, and ends of partial route B is set to be B1 and B2, respectively. Regarding final route, eights routes, that is, A1 to A2 to B1 to B2
A2 to A1 to B1 to B2
A1 to A2 to B2 to B1
A2 to A1 to B2 to B1 and opposite pattern of the above-mentioned can be assumed. In Step 4 shown in FIG. 8, among them, a route whose connecting distance of ends is considered to be the shortest and whose evaluation function J is considered to be small, the route of A1 to A2 to B1 to B2 is drawn.

A scanning candidate route extracting unit 22 can extract plural scanning candidate routes according to the following. As described in FIG. 4, a route is extracted in priority to technique in which one zigzag route is used as a base so as to make remaining spots to be a loop route, further, as described in FIG. 8, plural zigzag routes are extracted, and by connecting the plural zigzag routes in series, plural scanning candidate routes can be extracted.

As above mentioned, regarding the extracted plural scanning candidate routes, a value of evaluation function J which was described in Embodiment 1 is calculated, and a route whose value of evaluation function J is smallest is determined as a scanning route in a case where an affected part of a patient is irradiated. Accordingly, by decreasing the number of scanning candidate routes, a particle beam therapy system, in which scanning time is short, irradiation risk to normal tissue, especially important internal organ in normal tissue is small, can be obtained.

Further, within the scope of this invention, embodiments can be appropriately converted or omitted.

REMARKS

2. charged particle beam
5. X-directional scanning electromagnet
6. Y-directional scanning electromagnet
7. scanning electromagnet
8. target (affected part)
10. irradiation control device
11. scanning control unit
20. treatment planning device
21. spot position storing unit
22. scanning candidate route extracting unit
23. scanning route evaluating unit
24. scanning route determining unit
83. important internal organ

The invention claimed is:

1. A treatment planning device by which a scanning route of a charged particle beam of a particle beam therapy system is determined, wherein the particle beam therapy system comprises an X-directional scanning electromagnet and a Y-directional scanning electromagnet for deflecting a charged particle beam in an X-direction and a Y-direction which are two perpendicular directions to a traveling direction of the charged particle beam so as for the charged particle beam to move and stay repeatedly and the charged particle beam is irradiated onto an affected part of a patient which is an irradiation objective, wherein the treatment planning device comprises
a spot position storing unit which stores spot positions which are arranged in a grid shape in the X-direction and the Y-direction for each layer, which are points set in the affected part where the charged particle beam stays,
a scanning candidate route extracting unit which extracts plural candidates of scanning routes in which each of the scanning routes connects all spot positions in one layer which are stored in the spot position storing unit, a scanning route evaluating unit which evaluates each scanning route based on time which is required for scanning the charged particle beam in each scanning route of the plural candidates which are extracted by the scanning candidate route extracting unit, and a scanning route determining unit which determines a scanning route which is used for therapy based on a result which is evaluated by the scanning route evaluating unit.

2. The treatment planning device according to claim 1, wherein the scanning candidate route extracting unit sets a zigzag route as the scanning route by performing a route-setting repeatedly in which among arranging direction of spot positions which are arranged in a grid shape, among speed of the charged particle beam which is moved by the X-directional scanning electromagnet and speed of the charged particle beam which is moved by the Y-directional scanning electromagnet, a direction of faster speed is set to be a row direction, among rows of arrangement of the spot positions, a spot position of one end of one end row is set to be a starting point, a route is set from the starting point to a spot position of another end of the row, further, a route is set from a spot position of the other end to a spot position of an end of an adjacent row, further, a route is set from a spot position of an end of the adjacent row to another end of the row.

3. The treatment planning device according to claim 2, wherein the scanning candidate route extracting unit sets a loop route or other zigzag route in a group of spot positions where spot positions cannot be connected in a case where all spot positions in the one layer cannot be connected by the zigzag route.

4. The treatment planning device according to claim 3, wherein the scanning candidate route extracting unit sets a loop route which is set by a round-trip route in the spot position which is arranged in one dimension in a case where all spot positions in the one layer cannot be connected by a zigzag route or a loop route and a group of spot positions which is arranged in one dimension is left.

5. A particle beam therapy system comprising the treatment planning device claimed in claim 1, an X-directional electromagnet and a Y-directional electromagnet, an irradiation controlling device comprising a scanning control unit which controls the X-directional electromagnet and the Y-directional electromagnet according to a scanning route which is determined by the scanning route determining unit.

6. A method for determining a scanning route of a charged particle beam of a particle beam therapy system in which scanning is performed by moving and staying the charged particle beam repeatedly by an X-directional scanning electromagnet and a Y-directional scanning electromagnet for deflecting a charged particle beam in an X-direction and a Y-direction which are two perpendicular directions to a traveling direction of the charged particle beam and the charted particle beam is irradiated onto an affected part of a patient which is an irradiation objective, comprising a spot positions storing step for storing spot positions which are arranged in a grid shape in the X-direction and the Y-direction for each layer, which are points set in the affected part where the charged particle beam stays, a scanning candidate route extracting step for extracting plural candidates of scanning routes in which each of the scanning routes connects all spot positions in one layer which are stored in the spot position storing step, a scanning route evaluating step for evaluating each scanning route based on time which is required for scanning the charged particle beam in each scanning route of the plural candidates which are extracted by the scanning candidate route extracting unit, and a scanning route determining step for determining a scanning route which is used for therapy based on a result which is evaluated in the scanning route evaluating step.

7. The method for determining a scanning route of a charged particle beam according to claim 6, wherein in the scanning candidate route extracting step, a zigzag route as the scanning route is set by performing a route-setting repeatedly in which route setting in which among arranging direction of spot positions which are arranged in a grid shape, among speed of the charged particle beam which is moved by the X-directional scanning electromagnet and speed of the charged particle beam which is moved by the Y-directional scanning electromagnet, a direction of faster speed is set to be a row direction, among rows of arrangement of the spot positions, a spot position of one end of one end row is set to be a starting point, a route is set from the starting point to a spot position of another end of the row, further, a route is set from a spot position of the other end to a spot position of an end of an adjacent row, further, a route is set from a spot position of an end of the adjacent row to another end of the row.

8. The method for determining a scanning route of a charged particle beam according to claim 7, wherein in the scanning candidate extracting step, in a case where all spot positions in the one layer cannot be connected by the zigzag route, in the spot positions which cannot be connected, a loop route and other zigzag route are set.

9. The method for determining a scanning route of a charged particle beam according to claim 8, wherein in the scanning candidate extracting step, in a case where all spot positions in the one layer cannot be connected by a zigzag route or a loop route and a group of spot positions which are arranged in one dimension is left, in the group of spot positions which are arranged in one dimension, a loop route is determined by a round-trip route.

* * * * *